United States Patent [19]
Sandstrom et al.

[11] Patent Number: 5,512,480
[45] Date of Patent: Apr. 30, 1996

[54] FLOW-THROUGH BIOREACTOR WITH GROOVES FOR CELL RETENTION

[75] Inventors: Craig Sandstrom, Deerfield; E. T. Papoutsakis; William M. Miller, both of Evanston; James G. Bender, Lindenhurst, all of Ill.

[73] Assignees: Baxter International Inc., Deerfield; Northwestern Univ., Evanston, both of Ill.

[21] Appl. No.: 457,888

[22] Filed: Jun. 1, 1995

Related U.S. Application Data

[63] Continuation of Ser. No. 209,660, Mar. 11, 1994.

[51] Int. Cl.$^6$ .............................. C12M 3/00; C12M 1/00; C12M 1/24
[52] U.S. Cl. ................... 435/289.1; 435/813; 435/293.1; 435/299.1; 435/304.2; 220/670
[58] Field of Search ................................... 435/284, 287, 435/813, 296; 220/670

[56] References Cited

U.S. PATENT DOCUMENTS

| | | | |
|---|---|---|---|
| 3,853,712 | 12/1974 | House et al. | 435/289 |
| 4,514,499 | 4/1985 | Noll | 435/240.23 |
| 4,760,028 | 7/1988 | deBruyne et al. | 435/316 |
| 4,906,439 | 3/1990 | Grenner | 422/56 |
| 4,906,577 | 3/1990 | Armstrong et al. | 435/313 |
| 4,939,151 | 7/1990 | Bacehowski et al. | 435/284 |
| 4,963,489 | 10/1990 | Naughton et al. | 435/240.1 |
| 5,002,890 | 3/1991 | Morrison | 435/286 |
| 5,010,013 | 4/1991 | Serkes et al. | 435/285 |
| 5,084,393 | 1/1992 | Rogalsky | 435/284 |
| 5,151,366 | 9/1992 | Serkes et al. | 436/285 |
| 5,160,490 | 11/1992 | Naughton et al. | 435/284 |
| 5,223,428 | 6/1993 | Rose | 435/240.242 |
| 5,240,854 | 8/1993 | Berry et al. | 435/284 |
| 5,256,570 | 10/1993 | Clyde | 435/285 |
| 5,264,344 | 11/1993 | Sneath | 435/7.32 |
| 5,270,205 | 12/1993 | Rogalsky | 435/285 |
| 5,272,084 | 12/1993 | O'Connell et al. | 435/240.243 |

FOREIGN PATENT DOCUMENTS

| | | |
|---|---|---|
| 046681 | 8/1981 | European Pat. Off. . |
| 345415 | 2/1989 | European Pat. Off. . |
| WO 90/15877 | 12/1990 | WIPO . |
| WO 91/18972 | 12/1991 | WIPO . |
| WO 92/10564 | 6/1992 | WIPO . |
| WO 92/11355 | 7/1992 | WIPO . |

OTHER PUBLICATIONS

Chilukuri, R. et al. "Circulation, Diffusion, and Reaction within a Liquid Trapped in a Cavity", *Chem. Eng. Commun.* 22:127–138 (1983).

Higdon, J. "Stokes flow in arbitrary two-dimensional domains: shear flow over ridges and cavities", *J. Fluid Mech.* (1985) 159:195–226.

Chilukuri, R. et al., "Cleaning of rough rigid surface: Removal of a dissolved contaminant by convection-enhanced difusion and chemical", *J. Electrochem. Soc.: Solid State Science and Technology* May 1994.

Tighe, S. et al., "An experimental study of convection–aided removal of a contaminant from a cavity in a surface", *Chem. Eng. Commun.* 33:149–157 (1985).

*Primary Examiner*—Donald E. Czaja
*Assistant Examiner*—Jane Williams Elkin
*Attorney, Agent, or Firm*—Janice Guthrie; Michael Schiffer

[57] ABSTRACT

The invention is a flow-through bioreactor for the retention and culture of cells in perfused media. The bioreactor is a generally rectangular vessel with inlet and outlet ports in the lid allowing for media flow along the longitudinal axis of the vessel. The inner surface of the bottom wall of the bioreactor has a plurality of generally rectangular grooves having a length, a depth, and a width. The grooves are positioned in the bottom wall such that their length is transverse to the longitudinal axis of the vessel, allowing media flow across the width of the grooves. Cells settle into the grooves, where they proliferate and differentiate, without entering the bulk flow of media through the vessel, thus avoiding loss of cells due to media flow. The preferred grooves have a width to depth ratio of about 1:1 or 2:1. The preferred width of the grooves is about 50 μm to about 5,000 μm, and the preferred depth is about 50 μm to about 5,000 μm.

8 Claims, 1 Drawing Sheet

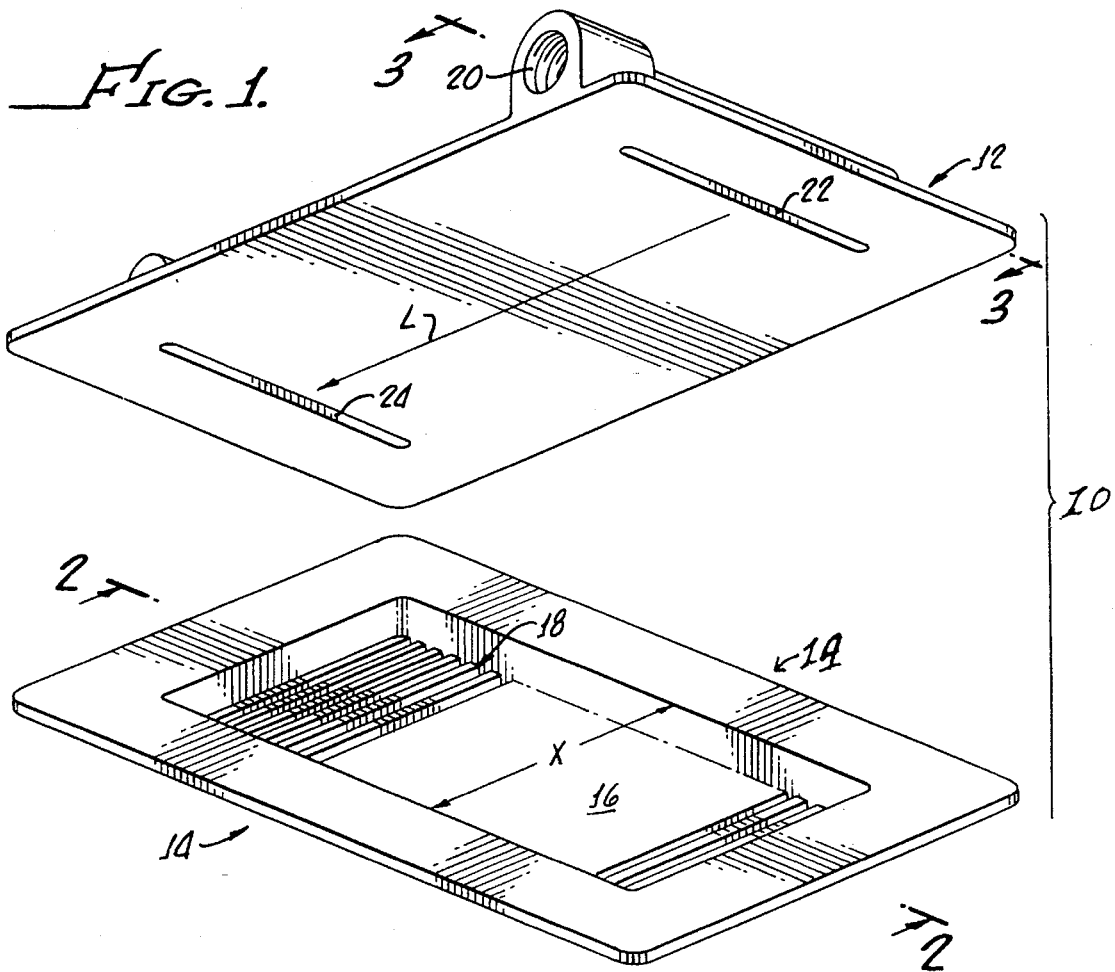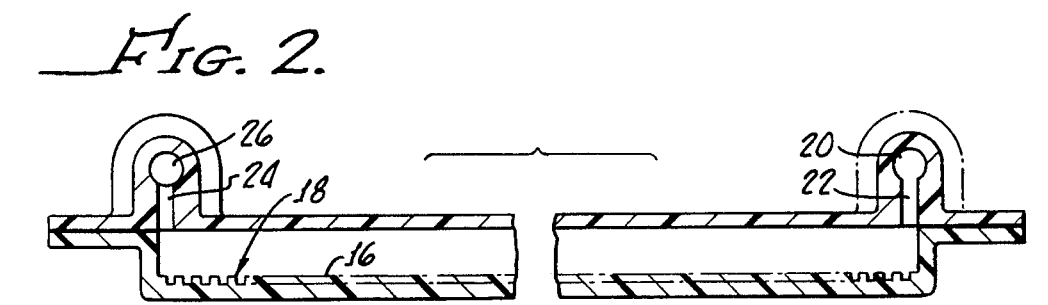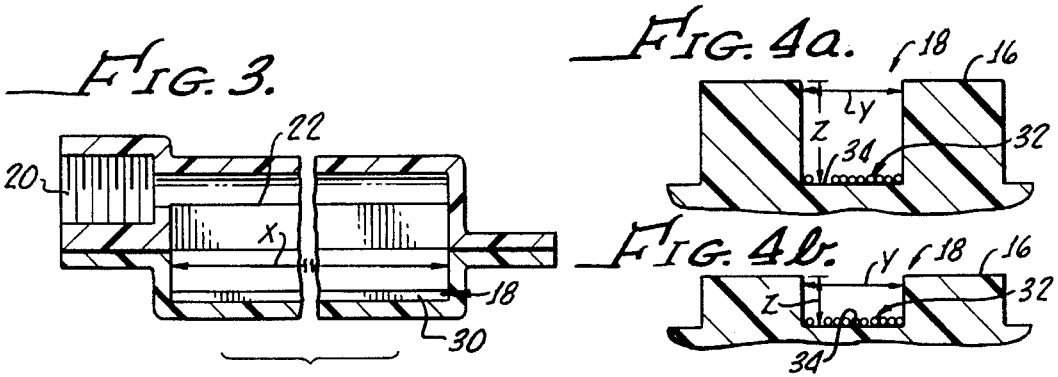

FLOW-THROUGH BIOREACTOR WITH GROOVES FOR CELL RETENTION

This is a continuation of application Ser. No. 08/209,660, filed Mar. 11, 1994.

BACKGROUND OF THE INVENTION

1. Technical Field

The present invention is in the field of bioreactors for cell culture. More specifically, the invention is in the field of bioreactors which allow for flow-through of media while retaining non-adherent as well as adherent cells within the bioreactor chamber.

2. Related Technology

In cell culture, it is often desirable to maintain cells in vitro for an extended time, during which the cells produce waste, acidify the medium, and use up nutrients from the medium. The exhaustion of the medium is accelerated when the cells proliferate and/or differentiate into highly metabolic cell types. Thus a central problem in cell culture is providing a means to refresh the culture medium without disturbing the cells.

Cell types which adhere to the surface of a culture flask may have their media exchanged or refreshed by simply pouring off the spent media and pouring in fresh media. Alternatively, a portion of the spent media may be gently drawn off and replaced with fresh media. Perfusion or flow-through of fresh media may be desirable for the growth of adherent cell types which require frequent or constant refreshment of culture media. However, even adherent cells may be adversely affected by the shear stress inflicted by the bulk flow of media. Adherent cells may be forced away from their moorings by the bulk media flow, and then lost from the culture system. Alternatively, adherent cells may stay attached to their substrate, but be adversely affected by the force of the fluid such that they fail to proliferate and/or differentiate. Part of the adverse effects of perfusion cultures may be attributed to dilution and wash out of factors produced by the cells themselves, when those factors are necessary for cell development.

Cell types which do not adhere to surfaces, but rather grow in suspension, present an extra challenge for media exchange. The problem is to exchange the media without losing a high proportion of the cells in the spent media.

Non-adherent cells may be retained in bioreactors with the use of physical barriers. A physical barrier may be in the form of a membrane that creates a barrier to the passage of cells, but allows the diffusion of nutrients and metabolic byproducts.

Hollow fiber bioreactors work on the principle of physical barriers. In a hollow fiber bioreactor, the cells are retained behind a semi-permeable membrane (i.e., the fiber material). A typical hollow fiber unit contains thousands of individual hollow fibers. Commonly, the cells are cultured in the spaces surrounding the fibers. Culture media is perfused through the spaces, and metabolic byproducts diffuse through the semi-permeable membrane, into the hollow fibers, and then out of the system. Examples of hollow fiber bioreactors are disclosed in WO 91/18972 (Knazek) and WO 92/10564 (Culver).

Other types of bioreactors are based on the use of semi-permeable membranes or supports (U.S. Pat. No. 5,264,344 (Sneath) and U.S. Pat. No. 5,223,428 (Rose).

The roller-bottle type of bioreactor is designed for even distribution of medium throughout the cell population. Traditionally, cells adhere to the inner surface of the bottle, which is constantly rotated to bathe the cells. Certain roller-bottle bioreactors have increased inner surface area provided by support strips or corrugations (U.S. Pat. No. 5,010,013 (Serkes); EP 345 415 (Tyndorf); U.S. Pat. No. 3,853,712; U.S. Pat. No. 5,270,205 (Rogalsky); U.S. Pat. No. 5,256,570 (Clyde)).

Other types of bioreactors, known as stirred bioreactors, often include the use of spin-filters and settling tubes in order to retain cells (U.S. Pat. No. 4,760,028 (deBruyne); U.S. Pat. No. 4,906,577 (Armstrong)). Anchorage-dependent cells may be grown on microcarrier beads, which are commonly used in stirred bioreactors (EP 046,681 (Tolbert); U.S. Pat. No. 5,002,890 (Morrison)).

Several types of static culture flasks make use of corrugations, ridges, or bristles on their internal surfaces in order to provide increased surface area for the growth of anchorage dependent cells (U.S. Pat. No. 5,084,393 (Rogalsky); U.S. Pat. No. 5,272,084 (O'Connell); U.S. Pat. No. 5,151,366 (Serkes)). U.S. Pat. No. 4,939,151 (Bacehowski) discloses a cell culture bag having a non-smooth inner surface to prevent the inner surfaces from sticking together during manufacturing and sterilization processes. A three-dimensional solid matrix has also been proposed for growing adherent cells (U.S. Pat. No. 4,514,499 (Noll)).

Researchers have had the most experience to date culturing certain specific types of cells, including bacteria, antibody producing hybridomas, fibroblasts, and eukaryotic cell lines. Other types of cells, such as hematopoietic cells, present unusual challenges in the design of a suitable bioreactor.

For certain cancer treatments, it is desirable to culture hematopoietic cells in order to administer the cultured cells to a patient. Hematopoietic cells are obtained from a donor's or a patient's bone marrow or peripheral blood.

The starting cell suspension to be cultured may contain a variety of hematopoietic cells in various stages of differentiation. Alternatively, the cell suspension may first be subjected to certain selection processes, resulting in a starting cell sample highly enriched for stem cells, for instance. Stem cells are primitive hematopoietic cells which have the potential to differentiate into cells of all hematopoietic lineages, including granulocytes, lymphocytes, erythrocytes, and megakaryocytes. It is generally believed that stem cells require adherence to a substrate in order to proliferate and develop to a progenitor stage. However, the cells that have progressed to the progenitor stage, and beyond, are thought to be generally non-adherent because their in vivo micro-environment would be a moving fluid (blood), and they would not be adapted for adherence to a static surface. Thus a culture of hematopoietic cells may contain a variety of different cell types including adherent and non-adherent cells. To further complicate the picture, some of the non-adherent cells may adhere to other cells which, in turn, adhere to a surface.

Hematopoeitic cells present additional challenges because they are shear sensitive. Hematopoietic cells do not appear to grow well when suspended in spinner flask cultures. In attempts to provide a micro-evironment conducive to hematopoietic cell growth, growth surfaces have been provided with stromal layers. The stromal layer is generally selected to mimic the extracellular matrix in the bone marrow and consists of proteins such as collagen and fibronectin. Bioreactors which depend on the use of stroma are disclosed in WO 90/15877 (Emerson), WO 92/11355 (Emerson), EP 0 358 506 (Naughton), U.S. Pat. No. 5,160,490 (Naughton), and U.S. Pat. No. 4,963,489 (Naughton).

The use of stroma is disadvantageous for several reasons. First, it is time consuming to produce the stromal layer on a cell culture surface, and great care must be taken not to introduce contaminants into the culture vessels. Certain techniques for laying down stroma require the use of living cells, such as fibroblasts, which are different from the cell type to be cultured. The introduction of foreign cell types into a culture vessel complicates the task of culturing a hematopoietic cell suspension suitable for clinical use.

Accordingly, a primary object for this invention is to provide a bioreactor which allows for the exchange of media without undue perturbation or loss of the cultured cells.

Another object for this invention is to provide a bioreactor which permits retention of cells without the use of stroma.

Another object of this invention is to provide a flow-through bioreactor which permits cultured cells to be easily and efficiently recovered from the bioreactor chamber.

These and other objects and advantages of the present invention will be apparent from a reading of the following detailed description of exemplary preferred embodiments of the invention, taken in conjunction with the appended drawing Figures, in which the same reference numeral refers to the same feature throughout the drawing Figures, or to features which are analogous in structure or function. Dimensions of the grooves are identified as X, Y, and Z. The longitudinal axis of the entire bioreactor vessel is identified as L.

BRIEF DESCRIPTION OF THE DRAWING FIGURES

FIG. 1 provides a partially schematic front quarter perspective view of a flow-through bioreactor with grooves for cell retention, according to the present invention.

FIG. 2 provides a longitudinal cross-sectional view of the bioreactor of the invention.

FIG. 3 provides a cross-sectional view through the inlet port and along the length dimension of a groove.

FIG. 4 provides enlarged fragmentary cross-sectional views of the grooves. FIG. 4a shows a groove of one embodiment of the invention, in which each groove has a ratio of width:depth=1:1. FIG. 4b shows a groove of a different embodiment of the invention, in which each groove has a ratio of width:depth=2:1.

DETAILED DESCRIPTION OF EXEMPLARY PREFERRED EMBODIMENTS OF THE INVENTION

Viewing FIG. 1, the bioreactor vessel 10 is shown with the lid 12 expanded from the view of the receptacle 14, in order to show the details of the inner surface of bottom wall 16. In operation, the lid 12 is sealed to the receptacle 14 by means known in the present art. For instance, the lid 12 may be permanently sealed to the receptacle 14 by means of chemical bonds, or may be sealed by means of a gasket and clamp. Alternatively, the entire bioreactor vessel 10 may be molded in one piece. Preferably, the bioreactor vessel 10 is made of a clear plastic material such as polycarbonate, polysulfonate, acrylic, or polystyrene. The inner surface of the vessel 10 may also be coated with teflon or another polymer, or may have a negative charge added, according to the growth requirements of the particular cell type to be cultured.

The inner surface of bottom wall 16 is provided with a plurality of long rectangular grooves 18 in which cells are retained while culture medium flows along the longitudinal axis L of the receptacle 14, in a direction transverse to the length dimension X of the grooves 18. Grooves 18 are disproportionately enlarged in this figure for better illustration.

The lid 12 has an inlet port 20, for conveying liquid media through inlet slot 22. The media flows from inlet slot 22, along the longitudinal axis L through the bioreactor vessel 10, and out the outlet slot 24. Outlet slot 24 connects with an outlet port (26 in FIG. 2). The media flow is regulated by well known means such that the flow is even across the inner surface of bottom wall 16. One example of means to regulate flow is provided in experimental Example 1 below.

FIG. 2 provides a longitudinal cross-sectional view of above described elements: inlet port 20, inlet slot 22, outlet slot 24, outlet port 26, inner surface of bottom wall 16, grooves 18. In this figure, grooves 18 are disproportionately enlarged for better illustration, and groove detail has been omitted on portions of inner surface of bottom wall 16. However, in the preferred embodiment of the invention, grooves 18 are continuous across the inner surface of bottom wall 16.

Inlet port 20 is connected to a reservoir of fresh media which is maintained at a suitable physiological pH by means well known in the art of cell culture. Outlet port 26 may be shunted to a waste container, or the media exiting outlet port 26 may be refreshed by well known means and recirculated to inlet port 20.

FIG. 3 is a cross-sectional view of bioreactor 10 in dimension X (FIG. 1), through inlet port 20 and inlet slot 22. This sectional view runs the length of a groove 18, showing the length face 30 of a groove 18.

FIG. 4a is a cross-sectional view, perpendicular to dimension X (FIGS. 1 and 3), showing the dimensions of a groove 18 in one preferred embodiment of the invention. In this embodiment, the ratio of width Y to depth Z is about 1:1. Suitably, width Y and depth Z are each about 50 µm to about 5,000 µm. Preferably, width Y is about 200 µm and depth Z is about 200 µm. Using dimensions Y:Z=200 µm:200 µm, a monolayer of hematopoietic cells 32 (approximately 10 µm deep), resting on the groove bottom 34, would change the groove width to depth ratio by only about 5%.

Although the groove 18 is depicted with corners and edges forming sharp 90° angles, it is understood that within the scope of this invention, corners and/or edges of the grooves might be rounded to form arcs. Given the present disclosure, it is also understood that different types of groove geometries may be devised to achieve similar results.

FIG. 4b shows the dimensions of a groove 18 in a second preferred embodiment of the invention. In this embodiment, the ratio of width Y to depth Z is about 2:1.

The preferred groove dimensions are suitable for retention of cells 32, both adherent and non-adherent, when media flows along longitudinal axis L (see FIG. 1) over the inner surface of bottom wall 16, across the top of the groove 18 (FIG. 4). As will be demonstrated in experimental examples below, the bulk flow of media along longitudinal axis L over the inner surface of bottom wall 16 does not perturb cells 32 within the grooves 18. Both adherent and non-adherent hematopoietic cells are able to proliferate and differentiate in the grooves 18 of the bioreactor of the present invention. Under regulated flow conditions, there is no appreciable loss of cells due to wash out. The fact that the cells thrive demonstrates that nutrients, growth factors, and oxygen from the bulk flow of fresh media across the mouth of the grooves 18 enter the fluid in the grooves to maintain the cells. Moreover, the health of the cultured cells indicates that the cells' deleterious metabolic by-products such as $CO_2$ diffuse out of the fluid in the grooves 18, into the bulk flow of media across the inner surface of the bottom wall 16, and ultimately out of the bioreactor. Moreover, the fact that essentially no cells are lost indicates that the cells themselves do not exit the mouths of the grooves 18 to enter the bulk flow along the longitudinal axis L of the bioreactor vessel.

One might be led to consider whether the success of the bioreactor of the present invention could be partially explained by theoretical flow patterns (Higdon, J. L., 1985, *J Fluid Mech* 159:195–226; Chilukuri, R., et al., 1984, *J Electrochem Soc* 131:1169–1173; Tighe, S., et al., 1985, *Chem Eng Commun* 33:149–157; Chilukuri, R., et al., 1983, *Chem Eng Commun* 22:127–138). Without the complication of cells in the grooves, the external flow across the inner surface of the bottom wall 16 might be incapable of penetrating the small grooves 18 in the surface, and thus might not displace the media from the grooves. Also, without cells in the grooves, a circulatory flow or "eddy" might be induced within each groove such that dissolved nutrients and gases might be exchanged by diffusion between the media in the grooves and the media in the external flow. However, the presence of cells in the grooves renders theoretical predictions of flow impractical within the present state of the art of fluid dynamics.

Flow patterns within the working bioreactor of the present invention cannot be practically described using theoretical calculations. However, this does not diminish the importance of the discovery of the present bioreactor that permits the retention, proliferation, and differentiation of non-adherent cells as well as adherent cells. The application of the bioreactor of the present invention to the culture of hematopoietic cells will be described in the experimental examples below.

EXAMPLE 1

Culture of Peripheral Blood Cells in Flow-Through Grooved Bioreactor Compared With Stroma and Static Culture Perfusion cultures in the grooved bioreactor were compared with perfusion cultures on a stromal layer (no grooves). Control static cultures were performed in either a smooth surfaced flask (no grooves) or a flask with a stromal layer.

Methods: Peripheral blood cells were obtained from two clinical sources. These cells were "mobilized" from the bone marrow of cancer patients into their peripheral blood by treatment of the patients with chemotherapeutic agents and cytokines, and collected by apheresis. The cells were received by overnight shipment in RPMI-1640 with 5% serum either on ice or at room temperature. The mononuclear cells were obtained by Ficoll density gradient (1.077 gm/cm3) centrifugation (1200 rpm for 20 minutes). The mononuclear layer obtained was washed once with 1×Ca++ Mg++ free phosphate buffered saline (PBS). The peripheral blood mononuclear cells used in the bioreactor studies had between 1 and 3% CD34+ cells (stem cells).

Culture Media & Growth Factors: Human long term media (HLTM) is composed of McCoy's 5A medium supplemented with 1% MEM Vitamins, 1% 2 mM glutamine, 1% 1 mM sodium pyruvate, 1% MEM essential amino acids, 1% MEM amino acids, 1% 1M HEPES, 1% 100 μM monothioglycerol, 0.1% 40 mg/ml gentamicin sulfate (Gibco), 12.5% preselected heat inactivated fetal bovine serum and 12.5% preselected heat inactivated horse serum. Colony assay medium is composed of 0.8% methylcellulose in IMDM supplemented with 4 μg/ml gentamicin sulfate, 30% preselected heat inactivated fetal bovine serum, 5% bovine albumin (Armour Pharmaceuticals), 150 U/ml recombinant human interleukin 3 (rhIL-3, R&D Systems, Inc.), 40 ng/ml recombinant human interleukin-6(rhIL-6, Sandoz or R&D Systems, Inc.), 150 U/ml recombinant human granulocyte colony-stimulating-factor (rhG-CSF, Immunex), 200 U/ml recombinant human granulocyte-macrophage colony-stimulating-factor (rhGM-CSF, Immunex), and 10 U/ml recombinant human erythropoietin (rhEpo, Amgen). Growth factor supplemented HLTM using the bioreactor studies contained 150 U/ml rhIL-3, 40 ng/ml rhIL-6, 150 U/ml rhG-CSF and 50 ng/ml stem cell factor (SCF, Amgen). All of the reagents were obtained from Sigma unless otherwise specified.

Stroma: Bone marrow cultures were established as reported by Koller et al (*Exp Hematol* 20:264–270, 1992). Briefly, stromal cells subcultured from 2-week-old marrow cultures were used to form stromal feeder layers by inoculating into 3.75×7.5 cm rectangular polycarbonate dishes (Cole Parmer, Chicago Ill.) at $4×10^5$ cells/ml in 5 ml HLTM. Each dish contained a 3.75×7.5 Thermanox® slide (Nunc, naperville, Ill.) which served as the culture substratum. After a 24 hour incubation at 37° C. in 5% $CO_2$ in air, dishes were irradiated with a dose of 12 Gy from a $^{137}Cs$ source. The following day, cells to be cultured were seeded onto the irradiated stroma for static culture experiments. For stromal bioreactor experiments, the slides coated with stroma were rinsed and placed on the inner bottom surfaces of bioreactor vessels without grooves.

Bioreactor cultures. The culture chambers were constructed of polycarbonate plastic, the tubing and connectors were constructed of Teflon, and the tubing used in the peristaltic pump was made of silicone. The culture chambers had the following dimensions:

L: Chamber length: 3.00 in or 7.62 cm
W: Chamber width: 1.50 in or 3.81 cm
H: Chamber height: 0.21 in or 0.53 cm
Af: Flow cross section (H W) 0.32 in² or 2.03 cm²
V: Chamber volume (H L W) 0.95 in³ or 15.5 cm³

The grooved bioreactors of the present invention also had the following dimensions:

Y: Groove width: 200 μm
Z: Groove depth: 200 μm

All of the bioreactor parts were washed, sterilized, and reused except for the pump tubing. It is understood that, for clinical use, the bioreactor would be a single-use disposable. The sterile bioreactor was completely assembled in a 37° C. incubator (Stericult, Forma Scientific). The culture chambers were placed in a rack that kept the chambers at a uniform 10° angle from horizontal to encourage air bubbles to leave the system. HLTM was then circulated through the bioreactor to allow calibration of the pH and $dO_2$ probes. For these calibrations, the bioreactor was first equilibrated with $CO_2$ for the first point of the pH calibration. Second, the bioreactor was equilibrated with air for the second point of the pH calibration and for the $dO_2$ calibration. The bioreactor was then drained and injected with 30 ml of HLTM and 60 ml of HLTM supplemented with 2×growth factors and the pH controller set at 7.35±0.05. The media was almost entirely drained from the three culture chambers per bioreactor prior to the seeding of the cultures. The cultures were seeded by injecting 10.0 ml of $2 \times 10^5$ cells/ml mononuclear cell suspension injected each of the three chambers for each bioreactor. The cells were allowed to settle for 15 minutes, and then the pump was started at approximately 0.2 ml/min. and increased every 15 minutes to 0.5, 1.0, 1.5, 2.0 and finally 2.5 ml/min, At the same time, static control cultures were established in 100 mm polycarbonate petri dishes containing 20 ml of HLTM supplemented with the same growth factors. The bioreactors were fed 3x/week by the replacement of one-half of the culture media. The static cultures were fed every 5 days. One of the three weekly feedings for the bioreactors occurred at the same time as the static cultures, that is when a portion of the cultures were harvested.

The bioreactor flow rate was measured during each feeding and the pH measured with an external pH probe (Corning). Cell counts were performed on the media removed from the cultures using the Coulter Counter (Coulter Electronics). One chamber per bioreactor and one corresponding control culture was harvested on days 5, 10 and 15. The bioreactor cultures were harvested by draining the contents, rinsing once with 10 ml of phosphate buffered saline (PBS), rinsing once with 1xcell dissociation solution (Sigma), and the rinsing a second time with PBS. This was accomplished in the same manner as for the washout experiments. The control cultures were harvested with the same draining and rinsing schedules. The cell number remaining in the culture vessels was estimated by rinsing once with 10 ml of cetrimide and counting nuclei with a Coulter Counter. The harvested cell suspensions were concentrated by centrifugation (15 minutes at 1200 rpm) and resuspended in approximately 10 ml of fresh HLTM. Cell counts were performed with both a Coulter Counter and also a hemacytometer. The viability was determined by trypan blue dye exclusion during the hemacytometer counts. Colony assays were established at 1,000, 3,000, and 9,000 cells/ml for mononuclear cells and 500, 1,500, and 3,000 cells/ml for CD34+ cells. These assays were cultured at 37° C. in a fully humidified incubator with an atmosphere of 5% $CO_2$, 5% $O_2$ and the balance $N_2$. Colonies were scored using a 40x stereomicroscope (Nikon) on day 14. White colonies containing >50 cells were scored as colony-forming-units granulocyte-macrophage (CFU-GM), red colonies containing >50 cells were scored as burst-forming-unit erythroid (BFU-E), and mixed red and white colonies containing >50 cells were scored as colony-forming-units mixed (CFU-Mix).

Long-term culture initiating (LTC-IC) assays were established in 24-well tissue culture plates (Falcon) containing $1 \times 10^5$ irradiated (2,000 rad) allogeneic human bone marrow cells per well. The cells being assayed were seeded at $5 \times 10^4$ and $2 \times 10^5$ cells per well for the harvested mononuclear cells or $2.5 \times 10^4$ and $1 \times 10^5$ cells per well for the harvested CD34+ cells. Each well contained 2.0 ml of HLTM. The cultures are incubated at 33° C. in a fully humidified incubator with an atmosphere of 5% $CO_2$, 5% $O_2$ and the balance $N_2$. The cultures are feed once per week by the replacement of one-half of the media with fresh HLTM. The cultures were harvested after 5 weeks and colony assays established at 15,000 cells/ml. All colonies scored from these colony assays were considered LTC-IC colonies. Flow cytometry was conducted by staining CD33 (Becton Dickinson)/CD34, CD11b (Becton Dickinson)/CD15 (Becton Dickinson), CD11b (Becton Dickinson), and Gly A (Amak, Inc.) and analyzing by flow cytometry (FACSTAR).

The static cultures were fed by the replacement of one-half of the culture media every 5 days. In spite of care taken in feeding, this inevitably led to the loss of some cells, since most or all of the cells were non-adherent.

Results from 3 series of experiments are shown in Table 1 below:

Key to Table 1

Stroma: number of stromal cells initially seeded for stromal cultures.

PBMN cells: number of peripheral blood mononuclear cells initially seeded in both stromal and non-stromal cultures.

Flo-Grv: The flow-through grooved bioreactor of the present invention.

Flo-Strom: A flow-through bioreactor, without grooves, with a stroma-layered slide on the bottom.

Stat/Smooth: A static control culture, no stroma.

Stat/Strom: A static control culture, with stroma.

TABLE 1

PBE #9 Summary (n = 3)

| Day | Cells | Hemacytometer | | CFU-Mix Assay | | LTC-IC Assay | |
| --- | --- | --- | --- | --- | --- | --- | --- |
| | | Cells | ±Cells | CFU-c | ±CFU-c | CFU-c | ±CFU-c |
| −1 | Stroma | 1,997,883 | 4,469 | #DIV/0I | #DIV/0I | #DIV/0I | #DIV/0I |
| 0 | PBMN Cells | 2,059,650 | ±114,665 | 16,276 | ±5,018 | 3,522 | ±1,390 |
| 5 | Flo/Grv | 1,600,333 | ±1,309,649 | 56,141 | ±27,399 | 750 | ±466 |
| 5 | Flo/Strom | 4,005,917 | ±3,719,435 | 64,934 | ±44,772 | 1,158 | ±768 |
| 5 | Stat/Smooth | 1,037,167 | ±102,098 | 59,725 | ±25,471 | 383 | ±152 |
| 5 | Stat/Strom | 1,488,250 | ±251,706 | 95,358 | ±69,265 | 745 | ±370 |
| 10 | Flo/Grv | 5,211,500 | ±1,911,085 | 204,840 | ±50,367 | 1,226 | ±406 |
| 10 | Flo/Strom | 5,854,000 | ±2,116,989 | 174,193 | ±50,403 | 575 | ±500 |
| 10 | Stat/Smooth | 4,984,000 | ±1,312,589 | 135,262 | ±14,930 | 330 | ±146 |
| 10 | Stat/Strom | 6,304,750 | ±2,339,924 | 189,850 | ±118,865 | 335 | ±191 |
| 15 | Flo/Grv | 19,842,500 | ±9,268,737 | 119,116 | ±70,766 | 2,263 | ±1,940 |
| 15 | Flo/Strom | 21,751,167 | ±2,985,267 | 174,705 | ±74,522 | 1,190 | ±482 |
| 15 | Stat/Smooth | 14,732,833 | ±2,700,869 | 94,865 | ±80,835 | 389 | ±398 |
| 15 | Stat/Strom | 9,683,750 | ±2,283,539 | 65,351 | ±38,100 | 417 | ±502 |

TABLE 1-continued

PBE #9 Summary (n = 3)

| | | CFU-Mix Assay | | CFU-Mix Assay | | CFU-Mix Assay | |
|---|---|---|---|---|---|---|---|
| Day | Cells | CFU-GM | ±CFU-GM | BFU-E | ±BFU-E | CFU-Mix | ±CFU-Mix |
| −1 | Stroma | #DIV/0I | #DIV/0I | #DIV/0I | #DIV/0I | #DIV/0I | #DIV/0I |
| 0 | PBMN Cells | 10,505 | ±2,967 | 5,480 | ±3,366 | 291 | ±340 |
| 5 | Flo/Grv | 50,760 | ±26,184 | 5,363 | ±5,044 | 19 | ±32 |
| 5 | Flo/Strom | 61,178 | ±42,267 | 3,685 | ±4,990 | 71 | ±123 |
| 5 | Stat/Smooth | 57,187 | ±26,577 | 2,537 | ±2,603 | 0 | ±0 |
| 5 | Stat/Strom | 89,387 | ±66,207 | 5,796 | ±5,661 | 175 | ±302 |
| 10 | Flo/Grv | 204,013 | ±50,292 | 827 | ±752 | 0 | ±0 |
| 10 | Flo/Strom | 174,193 | ±50,403 | 0 | ±0 | 0 | ±0 |
| 10 | Stat/Smooth | 130,825 | ±21,466 | 4,437 | ±7,685 | 0 | ±0 |
| 10 | Stat/Strom | 187,809 | ±121,434 | 2,041 | ±3,535 | 0 | ±0 |
| 15 | Flo/Grv | 119,116 | ±70,766 | 0 | ±0 | 0 | ±0 |
| 15 | Flo/Strom | 174,705 | ±74,522 | 0 | ±0 | 0 | ±0 |
| 15 | Stat/Smooth | 94,774 | ±80,943 | 92 | ±159 | 0 | ±0 |
| 15 | Stat/Strom | 65,276 | ±38,230 | 75 | ±130 | 0 | ±0 |

| | | Hemacytometer | | | Hemacytometer | |
|---|---|---|---|---|---|---|
| Day | Cells | Viability | ±Viability | Cells | Viability | ±Viability |
| −1 | Stroma | #DIV/0I | #DIV/0I | PBMN Cells | #DIV/0I | #DIV/0I |
| 5 | Flo/Grv | 79% | ±24% | Flo/Strom | 85% | ±18% |
| 5 | Stat/Smooth | 91% | ±8% | Stat/Strom | 91% | ±3% |
| 10 | Flo/Grv | 87% | ±10% | Flo/Strom | 78% | ±26% |
| 10 | Stat/Smooth | 97% | ±2% | Stat/Strom | 92% | ±3% |
| 15 | Flo/Grv | 95% | ±1% | Flo/Strom | 88% | ±9% |
| 15 | Stat/Smooth | 95% | ±4% | Stat/Strom | 93% | ±2% |

Cell number: The static cultures and the flow-through cultures contained similar cell and colony numbers up to day 10, during which time the cell numbers were relatively low. At day 15, when the cell numbers were relatively high, the performance of the static cultures dropped and the flow-through cultures excelled. Comparing results from both types of flow-through bioreactors at day 15, the number of cells in the grooved bioreactor was comparable to the number of cells in the bioreactor with stroma (no grooves). These results indicate that for cell retention and proliferation the grooved bioreactor performs as well as a bioreactor with stroma at all time points tested.

Colony-forming units: Cultures from the grooved bioreactor contained a number of granulocyte-macrophage/colony-forming units (CFU-GM) comparable to cultures from the stroma-layered bioreactor at all time points. After day 5, few erythroid cells and few BFU-E were detected in any of the cultures because the cytokine mix in the media was designed to drive granulocyte/macrophage differentiation, and not erythropoiesis.

Long-term colony intiating cells: Cultures from both types of bioreactors contained comparable numbers of long-term colony intiating cells at all time points.

Viability: Cells from both types of bioreactors contained comparable number of viable cells at all time points. The viability of recovered cells was very good, ranging from 79–97%.

EXAMPLE 2

Culture of CD34+ Hematopoietic Stem Cells in the Grooved Bioreactor

Within the art of hematopoietic cell culture, it is a general belief that a proportion of CD34+ cells are stem cells which may require adherence to a substrate, or stroma. Therefore, it was of interest to determine whether CD34+ selected cells could proliferate in the grooves of the bioreactor of the present invention. There is no stroma in the bioreactor of the present invention. It is understood that the bioreactor could be formed of different types of plastics, or have plastic surfaces treated such that cells could adhere. However, the bioreactor used in the following experiments was formed of a type of plastic, polycarbonate, which is thought to be non-conducive to cell adherence since its surface is neutrally charged.

Peripheral blood samples were obtained and mononuclear cell suspensions were prepared as described in Example 1 above. Phenotypic analysis of the starting samples by flow cytometry showed that the peripheral blood samples originally contained 1–3% CD34+ cells. CD34+ cells were selected from the mononuclear cell suspension by first incubating the suspension with mouse monoclonal antibodies against CD34, which bound specifically to the CD34 cell surface antigen on CD34+ cells. Then paramagnetic beads coated with sheep-anti-mouse antibodies were incubated with the cell suspension. The paramagnetic beads then bound the CD34+ cells via binding of the sheep-anti-mouse antibodies to the mouse antibodies on the CD34+ cells, to form bead/CD34+ cell complexes. The bead/CD34+ cell complexes were then selected from the total cell population by magnetic attraction. After washing, the CD34+ cells were released from the beads by enzymatic digestion with chymopapain.

The CD34+ cells were seeded into bioreactor and static control cultures as described in Example 1 above, except none of the cultures had stromal layers.

Experiments using mononuclear cell preparations, unselected for CD34+ cells, were conducted in parallel with the CD34+ experiments.

Results are shown in Table 2 below:

Key for Table 2

PBMN Cells: Number of peripheral blood mononuclear cells initially seeded.

CD34+ Cells: Number of CD34+ selected cells initially seeded.

MNC/Grv: Unselected, peripheral blood mononuclear cells cultured in grooved bioreactor of the present invention.

CD34+/Grv: CD34+ selected cells cultured in grooved bioreactor of the present invention.

MNC/stat: Unselected, peripheral blood mononuclear cells in static culture.

CD34+/stat: CD34+ selected cells in static culture.

colony initiating cells within the grooved bioreactor cultures stayed relatively constant from day 5 through day 15. Viability within all cultures was very good, ranging from 89–98%.

In conclusion, the grooved bioreactor of the present invention successfully retained cells under perfused media conditions, and performed as well as or better than a flow-through bioreactor with a stromal layer, but without grooves. Moreover, the retained cells proliferated and differentiated into colony-forming units and long-term colony forming cells. Both peripheral blood mononuclear cells and CD34+ selected cells successfully proliferated and differentiated within the grooves of the flow-through bioreactor of the present invention.

TABLE 2

PBE #10-1, 2 & 4

| Day | Cells | Hemacytometer | | Colony Assay | | LTC-IC Assay | |
|---|---|---|---|---|---|---|---|
| | | Cells | ±Cells | CFU-c | ±CFU-c | LTC-IC | ±LTC-IC |
| 0 | PBMN Cells | 2,075,000 | ±417,582 | 9,038 | ±4,806 | 1,260 | ±1,309 |
| 0 | CD34 + Cells | 199,383 | ±53,104 | 4,953 | ±2,426 | 2,411 | ±505 |
| 5 | MNC/Grv | 1,550,750 | ±189,591 | 67,433 | ±39,939 | 1,503 | ±1,520 |
| 5 | CD34+/Grv | 504,333 | ±233,552 | 52,776 | ±24,550 | 1,258 | ±921 |
| 5 | MNC/stat | 1,531,278 | ±437,718 | 81,648 | ±43,788 | 1,134 | ±980 |
| 5 | CD34+/stat | 334,194 | ±259,452 | 47,995 | ±44,406 | 555 | ±522 |
| 10 | MNC/Grv | 6,313,111 | ±5,779,192 | 129,670 | ±121,940 | 1,481 | ±1,796 |
| 10 | CD34+/Grv | 4,267,111 | ±3,939,473 | 132,330 | ±101,548 | 847 | ±1,122 |
| 10 | MNC/Stat | 8,218,111 | ±9,565,528 | 236,567 | ±236,435 | 600 | ±996 |
| 10 | CD34+/Stat | 2,290,556 | ±3,244,993 | 121,601 | ±210,123 | 249 | ±421 |
| 15 | MNC/Grv | 14,517,444 | ±16,218,689 | 90,933 | ±51,990 | 1,395 | ±1,963 |
| 15 | CD34+/Grv | 22,321,556 | ±9,115,309 | 86,479 | ±41,362 | 1,600 | ±828 |
| 15 | MNC/Stat | 13,259,944 | ±11,429,621 | 101,945 | ±99,503 | 160 | ±142 |
| 15 | CD34+/Stat | 14,225,511 | ±12,269,548 | 58,964 | ±62,046 | 1,408 | ±1,158 |

| Day | Cells | Colony Assay | | Colony Assay | | Colony Assay | |
|---|---|---|---|---|---|---|---|
| | | CFU-GM | ±CFU-GM | BFU-E | ±BFU-E | CFU-Mix | ±CFU-Mix |
| 0 | PBMN Cells | 8,599 | ±4,059 | 439 | ±760 | 0 | ±0 |
| 0 | CD34 + Cells | 4,937 | ±2,410 | 16 | ±28 | 0 | ±0 |
| 5 | MNC/Grv | 67,433 | ±39,939 | 0 | ±0 | 0 | ±0 |
| 5 | CD34+/Grv | 52,776 | ±24,550 | 0 | ±0 | 0 | ±0 |
| 5 | MNC/Stat | 81,648 | ±43,788 | 0 | ±0 | 0 | ±0 |
| 5 | CD34+/Stat | 47,995 | ±44,406 | 0 | ±0 | 0 | ±0 |
| 10 | MNC/Grv | 129,516 | ±122,032 | 153 | ±266 | 0 | ±0 |
| 10 | CD34+/Grv | 132,330 | ±101,548 | 0 | ±0 | 0 | ±0 |
| 10 | MNC/Stat | 236,567 | ±236,435 | 0 | ±0 | 0 | ±0 |
| 10 | CD34+/Stat | 121,601 | ±210,123 | 0 | ±0 | 0 | ±0 |
| 15 | MNC/Grv | 90,933 | ±51,990 | 0 | ±0 | 0 | ±0 |
| 15 | ICD34+/Grv | 86,479 | ±41,362 | 0 | ±0 | 0 | ±0 |
| 15 | MNC/Stat | 101,945 | ±99,503 | 0 | ±0 | 0 | ±0 |
| 15 | ICD34+/Stat | 58,964 | ±62,046 | 0 | ±0 | 0 | ±0 |

| Day | Cells | Hemacytometer | | Cells | Hemacytometer | |
|---|---|---|---|---|---|---|
| | | Viability | ±Viability | | Viability | ±Viability |
| 0 | PBMN Cells | 95.83% | 5.65% | CD34 + Cells | 97.41% | 2.26% |
| 5 | MNC/Grv | 95.81% | 1.50% | CD34+/Grv | 89.03% | 7.62% |
| 5 | MNC/Stat | 97.47% | 1.86% | CD34+/Stat | 89.52% | 8.30% |
| 10 | MNC/Grv | 95.33% | 4.22% | CD34+/Grv | 91.12% | 10.51% |
| 10 | MNC/Stat | 94.04% | 8.45% | CD34+/Stat | 91.56% | 6.56% |
| 15 | MNC/Grv | 97.81% | 0.82% | CD34+/Grv | 98.07% | 1.11% |
| 15 | MNC/Stat | 96.23% | 4.30% | CD34+/Stat | 92.15% | 12.51% |

Results: In terms of absolute cell number, the CD34+ cell cultures increased about 100 fold over 15 days in the grooved bioreactor of the present invention. In terms of colony-forming units, the cultures in the grooved bioreactor peaked at day 10; the slight decline in CFU at day 15 might have been due to a progression into more differentiated cell types which do not form colonies. The number of long-term

What is claimed is:

1. A flow through bioreactor for retention and culture of cells in a perfused media, said bioreactor comprising:
   a generally rectangular vessel having first and second opposite ends, said vessel formed by spatially separated top and bottom walls and four spaced apart side walls to define a generally rectangular chamber having a longitudinal axis running from said first to said second opposite ends, said vessel provided at said first opposite end with an inlet port which opens into said chamber and at said second opposite end with an outlet port which opens into said chamber, said inlet and outlet ports being configured to provide generally even flow of a media through said chamber in a direction generally parallel to said chamber longitudinal axis, said bottom wall provided with a plurality of generally rectangular grooves opening into said chamber, said grooves defined by a width, depth, and length, said length of said grooves running in a direction transverse to said chamber longitudinal axis allowing for media flowing in said direction generally parallel to said chamber longitudinal axis from said inlet to said outlet ports to traverse across said grooves, and said width and depth of said grooves being sufficient to maintain said cells in said grooves during the flow of said media.

2. The flow-through bioreactor of claim 1 wherein said grooves have a width to depth ratio of about 1:1.

3. The flow-through bioreactor of claim 2 wherein said grooves have a width of about 50 μm to about 5,000 μm and a depth of about 50 μm to about 5,000 μm.

4. The flow-through bioreactor of claim 3 wherein said grooves have a width of about 200 μm and a depth of about 200 μm.

5. The flow-through bioreactor of claim 1 wherein said grooves have a width to depth ratio of about 2:1.

6. The flow-through bioreactor of claim 1 wherein said vessel is arranged at an angle from the horizontal.

7. The flow-through bioreactor of claim 1 wherein said vessel chamber is arranged at an angle from the horizontal.

8. The flow-through bioreactor of claim 7 wherein said angle is about 10 degrees.

\* \* \* \* \*